(12) United States Patent
Ehr et al.

(10) Patent No.: US 6,193,744 B1
(45) Date of Patent: Feb. 27, 2001

(54) STENT CONFIGURATIONS

(75) Inventors: Timothy G. J. Ehr, Elk River; Graig L. Kveen, Maple Grove, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/151,053

(22) Filed: Sep. 10, 1998

(51) Int. Cl.[7] .................................................. A61F 2/06
(52) U.S. Cl. ............................. 623/1; 623/1.18; 623/1.15
(58) Field of Search .......................... 623/1, 12, 1.11, 623/1.12, 1.15, 1.18, 1.2, 13; 606/198

(56) References Cited

U.S. PATENT DOCUMENTS

| | | | |
|---|---|---|---|
| 5,776,183 | * | 7/1998 | Kanesaka et al. ................ 623/1 |
| 6,017,365 | * | 1/2000 | Von Oepen ........................ 623/1 |

FOREIGN PATENT DOCUMENTS

| | | |
|---|---|---|
| 29701 758 U1 | 3/1997 | (DE) . |
| 297 02 671 U1 | 4/1997 | (DE) . |
| 297 16 117 U1 | 2/1999 | (DE) . |
| 734 698 | 2/1996 | (EP) . |
| 97/09945 | 3/1997 | (WO) . |
| 97/14375 | 4/1997 | (WO) . |
| 97/26840 | 7/1997 | (WO) . |
| 97/32543 | 9/1997 | (WO) . |
| 97/40780 | 11/1997 | (WO) . |
| 98/07386 * | 2/1998 | (WO) ........................ A61F/2/06 |
| 98/32412 | 7/1998 | (WO) . |
| 98/40035 | 9/1998 | (WO) . |
| 98/44871 | 10/1998 | (WO) . |
| 99/17680 | 4/1999 | (WO) . |
| 99/39660 | 8/1999 | (WO) . |

* cited by examiner

*Primary Examiner*—Michael Buiz
*Assistant Examiner*—Anthony S. King
(74) *Attorney, Agent, or Firm*—Vidas, Arrett & Steinkraus

(57) ABSTRACT

Improved stent configurations exhibiting limited recoil, resistance to compression and improved longitudinal flexibility are disclosed. The stent comprised of a plurality of annular elements aligned to form a cylindrical stent body. The annular elements are comprised of a plurality of open, generally boomerang-shaped segments interconnected top-to-bottom around each of the annular elements. Adjacent annular elements are interconnected by interconnecting element.

24 Claims, 4 Drawing Sheets

STENT CONFIGURATIONS

BACKGROUND OF THE INVENTION

1. Field of the Invention

This invention relates to stents of improved configuration.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, etc. Some stents are self-expanding and some are expanded by an interior radial force.

SUMMARY OF THE INVENTION

This invention provides new configurations of the segments making up stents which may be adapted to all of the various types of prior art stents described above and/or known previously in the art. There are numerous advantages to the new configurations. For example, the configurations of the invention limit recoil and add resistance to compression for an expanded stent, among other things. Also, the stents of this invention are longitudinally flexible.

The inventive stents comprise a plurality of annular elements aligned to form a cylindrical stent body. Each annular element, in turn, is comprised of a plurality of open, generally boomerang-shaped segments. The segments are interconnected top-to-bottom around each of the annular elements. Adjacent annular elements are interconnected by one or more interconnecting elements. Each interconnecting element extends from an end of a boomerang-shaped segment in one annular element to an end of a boomerang-shaped segment in an adjacent annular element. In a preferred embodiment an interconnecting element extends from each boomerang-shaped segment in an annular element to a neighboring boomerang-shaped segment in an adjacent annular element.

Interconnecting elements joining adjacent annular elements are desirably U-shaped or zig-zag shaped, although other curvilinear and rectilinear interconnecting elements may also be used.

Adjacent boomerang-shaped segments in an annular element may be interconnected via a link extending from the top of a segment to the bottom of an adjacent segment. The links may range in design from a short, straight connector to any of the shapes described below for the interconnecting elements.

DETAILED DESCRIPTION OF THE PREFERRED EMBODIMENTS

Figure 1:
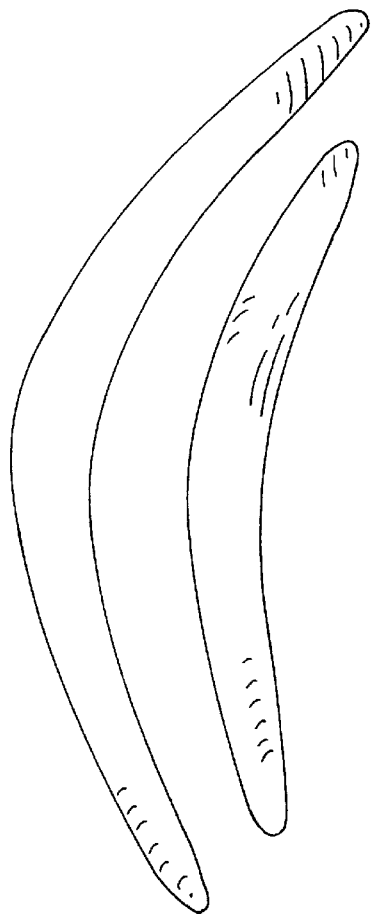
FIG. 1 is a schematic showing boomerang shapes.

For the purposes of this invention, the term boomerang is used to describe the shape of certain stent segments and is used in the sense as described in the *Websters New Collegiate Dictionary* with reference to FIG. 1 hereof:

"boomerang 1: A bent or angular throwing club which can be thrown so as to return near the starting point."

Figure 3:
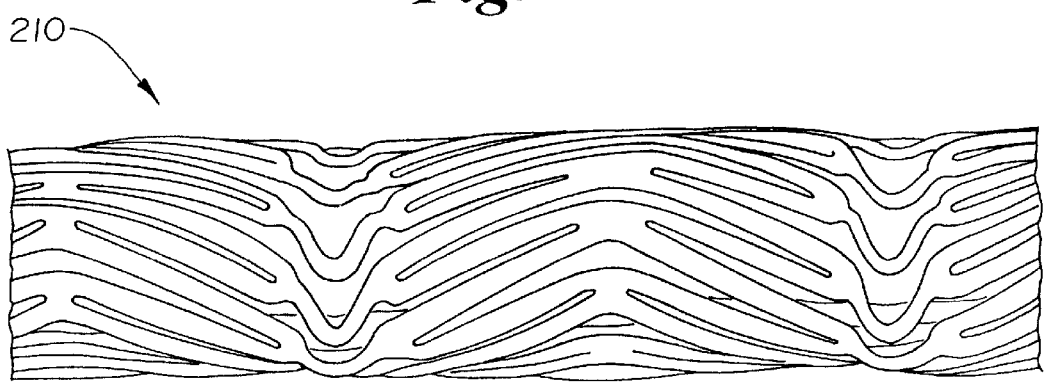
FIG. 3 is a longitudinal view of the stent of FIG. 2 in its normal tubular unexpanded condition.
Figure 2:
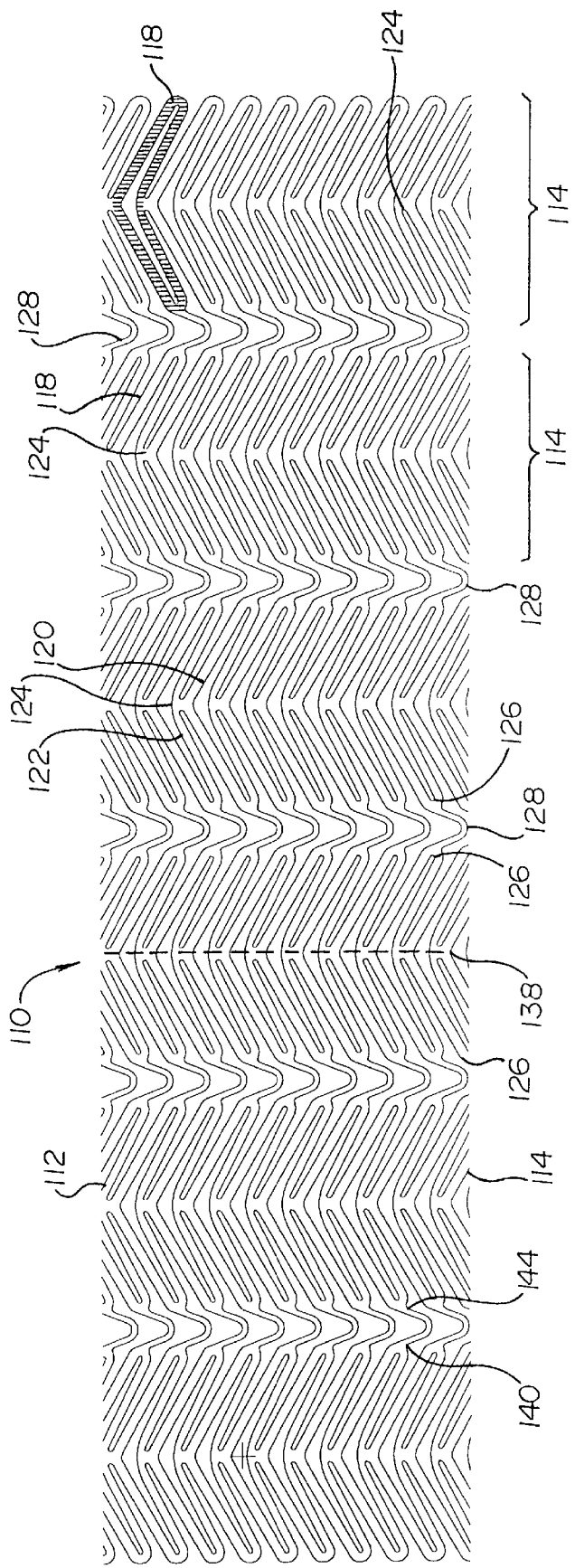
FIG. 2 is a flat plan view of an embodiment of a stent configuration of the invention in the unexpanded condition.
Figure 4:
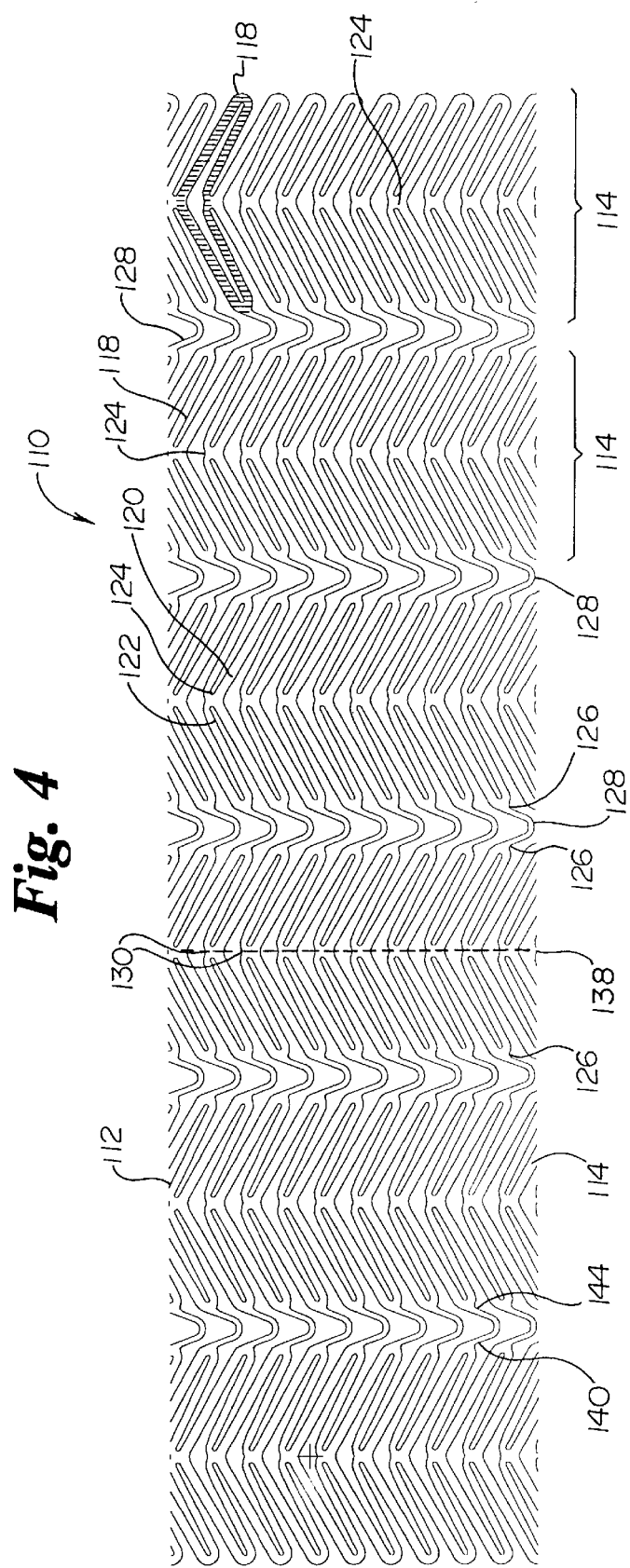
FIG. 4 is a flat plan view of an embodiment of a stent configuration of the invention in the unexpanded condition.

An embodiment of a generally cylindrical stent according to the invention is illustrated in the flat at 110 in FIG. 2 or FIG. 4. The stent may be formed of a metal tube such as nitinol, or stainless steel preferably, which has been etched or preferably laser cut to the configuration shown in the flat plan view of FIGS. 2 or 4. The configuration may be formed in flat sheet and rolled into a cylinder with a welded seam or the like joining together edges 112 and 114, or the configuration may be formed directly in a small tube such as a hypotube. A tubular form of the stent is shown generally at 210 in FIG. 3.

Figure 6:
FIG. 6 is an interconnecting element that may be used to join adjacent annular elements in another embodiment of the invention.

The configurations shown in FIGS. 2–4 are made up of a plurality of aligned annular elements 114 aligned as shown to provide a generally cylindrical stent body. Each annular element 114 is comprised of a series of generally boomerang shaped segments indicated at 118 (see darkened segment in the Figures for clarity) having an open structure joined top 120 to bottom 122 at segment junction 124. Segments 118 are arranged or networked as shown in the Figures with ends 126 of neighboring segments on adjacent annular elements joined by interconnecting elements 128. In FIGS. 2–4, interconnecting element 128 is a U-shaped element which is a partly open curve. Alternative interconnecting elements including zig-zag shaped element 228 as shown in FIG. 6, which may be used in place of U-shaped element 128 to join adjacent annular elements 114 together.

The configurations of FIGS. 2 and 4 are substantially similar to one another, differing principally in the presence of a dimple 130 in each bottom 122 of each segment 118 in the configuration of FIG. 4. Without being bound by a particular theory, it is believed that the presence of the dimple limits the extent to which the stent buckles out of the plane on expansion.

It is desirable that the boomerang-shaped segments be at least substantially symmetric about a midline 138 extending from the top 120 of the segment to the bottom 122 of the segment. Midline 138 is situated midway between ends 126 of the segment.

Figure 5:
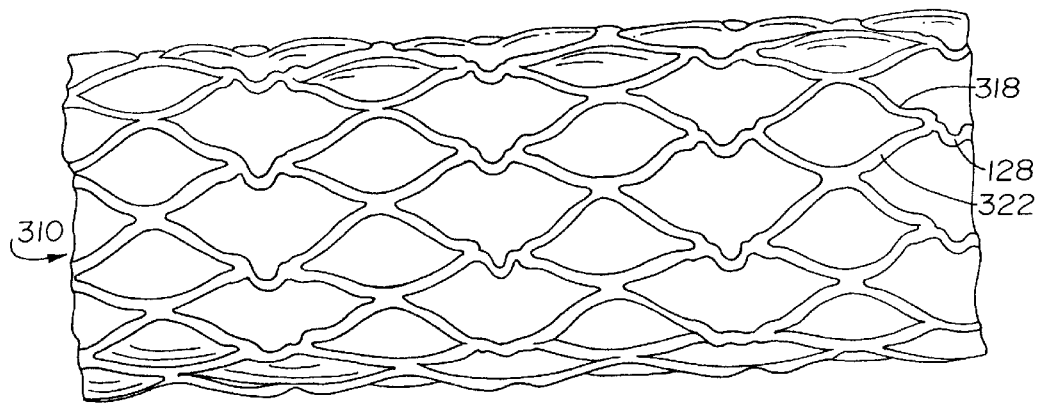
FIG. 5 is a longitudinal view of the stent of FIG. 3 in its tubular, expanded condition.

When the stent of FIG. 2 is expanded, as shown generally at 310 in FIG. 5 on a balloon for example, the boomerang-shaped segments 118 of the unexpanded stent take on a new configuration. The segments 318 take on the shape of rounded triangles with bulging bottoms 322.

It is desirable that the interconnecting elements be U-shaped as shown in FIGS. 2 and 4 or zig-zag shaped as shown in FIG. 6. However, in a more general sense, the invention contemplates the use of curvilinear as well as rectilinear interconnecting elements, including straight elements. Examples of other suitable connectors are disclosed in U.S. patent application Ser. No. 09/111,531 filed Jul. 8, 1998, U.S. patent application Ser. No. 08/846,164 filed Apr. 25, 1997, WO 97/32543 to Divysio Solutions LTD. and WO 97/40780 to David G. Jang, all of which are incorporated herein by reference. Of course, adjacent boomerang-shaped segments may also be joined side-by-side with a region of overlap between adjacent boomerang-shaped segments.

Figure 7:
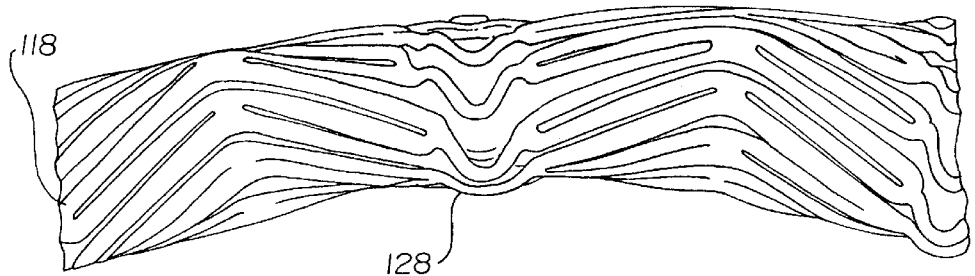
FIG. 7 is a view of the stent of FIG. 3 after being bent.

It is also desirable that interconnecting elements be flexible so as to accommodate bending of the stent without substantial distortion of the boomerang-shaped segments. FIG. 7 shows the stent of FIG. 3 having been bent. As shown in FIG. 7, as the stent is bent, interconnecting elements in tension open while interconnecting elements in compression close to accommodate bending of the stent.

Although as shown in the Figures an interconnecting element extends from each boomerang-shaped segment in an annular element to a nearest neighboring boomerang-shaped segment in an adjacent annular element, the invention further contemplates the possibility of an interconnecting element extending from each boomerang-shaped segment in an annular element to a next-nearest neighboring boomerang-shaped segment in an adjacent annular element. In the latter case, the first end 140 and second end 144 of each interconnecting element 128 would be circumferentially offset along the stent.

In a more general sense, the invention further contemplates a stent in which each adjacent annular element is interconnected by one or more interconnecting elements and each interconnecting element extends from an end of a boomerang-shaped segment in one annular element to an end of a boomerang-shaped segment in an adjacent annular element. As such, an interconnecting element need not extend from each boomerang-shaped segment. An example of this is a stent in which interconnecting elements extend from every second or third boomerang-shaped segment in an annular element.

The invention also contemplates the possibility of altering the orientation of some of the annular elements. In one such embodiment, adjacent annular elements in the flat pattern are rotated by 180° relative to one another so that adjacent annular elements point in opposite directions.

Although the ends of nearest neighboring segments in adjacent annular elements are shown in the figures as aligned with one another along the circumference of the stent, the invention further contemplates embodiments of the stent in which nearest neighboring segments in adjacent annular elements are circumferentially displaced relative to one another.

In yet another series of embodiments, adjacent (or non-adjacent) annular elements may be formed of different sized boomerang-shaped elements. As such, adjacent (or non-adjacent) annular elements may span different lengths. Alternatively, adjacent (or non-adjacent) annular elements may comprise different numbers of boomerang-shaped segments.

Although in the embodiment of FIGS. 2–4, segment junction 124 is shown as a small, straight link extending from the top of one segment to the bottom of an adjacent segment, the invention also contemplates the possibility of adjacent boomerang-shaped segments within an annular element being connected by U shaped links, zig-zag shaped links or any of the shapes disclosed above for the interconnecting elements. Additionally, other shaped segments may be interspersed among the boomerang-shaped segments.

The inventive stent may be self-expanding or mechanically expandable such as by balloon. The stent may be made of a variety of suitable bio-compatible materials including metal, plastic and any other material capable of functioning as an expandable stent. For example, the stent may be of metal wire or ribbon such as tantalum, stainless steel or the like or of metal sheeting or metal tubing. It may be thin-walled. It may be of shape memory alloy such as Nitinol or the like.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A generally cylindrical, radially expandable stent comprised of
   a plurality of annular elements aligned to form a cylindrical stent body,
      each annular element having
         a first end and
         a second end,
         the first end longitudinally offset from the second end,
      each annular element comprised of
         a plurality of separate boomerang-shaped segments,
         each boomerang segment having
            a top and
            a bottom,
            the top circumferentially offset from the bottom,
            the top and bottom interconnected at a first end and at a second end to define a closed perimeter with an opening therethrough,
         the boomerang segments interconnected top-to-bottom around the annular element, and
   a plurality of curvilinear interconnecting elements, each curvilinear interconnecting element extending from a first end of a boomerang segment in an annular element to a second end of a boomerang segment in an adjacent annular element.

2. The stent of claim 1 wherein each interconnecting element has one or more bends therein.

3. The stent of claim 2 wherein each interconnecting element is a U-shaped segment.

4. The stent of claim 2 wherein each interconnecting element is a zig-zag-shaped segment.

5. The stent of claim 1 made of metal.

6. The stent of claim 5 made of stainless steel.

7. The stent of claim 5 wherein the metal is a shape memory metal.

8. The stent of claim 1 wherein an interconnecting element extends from each boomerang-shaped segment in an annular element to a boomerang-shaped segment in an adjacent annular element.

9. The stent of claim 3 wherein an interconnecting element extends from each boomerang-shaped segment in an annular element to a neighboring boomerang-shaped segment in an adjacent annular element.

10. The stent of claim 1 wherein at least a portion of each interconnecting element is curvilinear.

11. The stent of claim 1 wherein each boomerang-shaped segment is symmetric about a midline extending from the top of the segment to the bottom of the segment, the midline situated midway between the ends of the segments.

12. The stent of claim 1 wherein each bottom has a dimple therein.

13. The stent of claim 1 made of a bio-compatible material.

14. The stent of claim 1 wherein each interconnecting element has a first end and a second end, the first end circumferentially offset from the second end.

15. The stent of claim 1 wherein the orientation of adjacent annular elements differs.

16. The stent of claim 1 wherein adjacent annular elements are oppositely oriented.

17. The stent of claim 1 including annular elements of different lengths.

18. The stent of claim 1 including annular elements having differing number of boomerang shaped segments.

19. The stent of claim 1 including boomerang segments of differing sizes.

20. The stent of claim 1 wherein nearest neighboring boomerang segments in adjacent annular elements are circumferentially offset.

21. The stent of claim 1 wherein circumferentially adjacent boomerang segments are joined together with a curvilinear element extending from the top of a boomerang segment to the bottom of an adjacent boomerang segment.

22. The stent of claim 1 wherein circumferentially adjacent boomerang segments are joined together with an element having one or more bends therein, the element extending from the top of a boomerang segment to the bottom of an adjacent boomerang segment.

23. A generally cylindrical, radially expandable stent comprised of
   a plurality of annular elements aligned to form a cylindrical stent body,
   each annular element comprised of a plurality of separate boomerang-shaped segments, each segment having a top and a bottom, the top circumferentially offset from the bottom, a first end and a second end, the top and bottom interconnected at the first and second ends to define an opening therethrough, adjacent segments in an annular element connected by a link extending from the top of a segment to the bottom of an adjacent segment,
   adjacent annular elements interconnected by one or more interconnecting elements, each interconnecting element extending from an end of a boomerang-shaped segment in one annular element to an end of a boomerang-shaped segment in an adjacent annular element.

24. A generally cylindrical, radially expandable stent comprised of
   a plurality of interconnected annular elements,
      each annular element having
         a first end and
         a second end,
         the first end longitudinally offset from the second end,
      each annular element comprised of
         a plurality of boomerang-shaped segments,
         each boomerang segment having
            a top and
            a bottom,
            the top circumferentially offset from the bottom,
            the top and bottom interconnected at a first end and at a second end to define a closed perimeter, each boomerang segment having an opening therethrough,
            the closed perimeter of circumferentially adjacent boomerang segments non-overlapping,
         the boomerang segments interconnected top-to-bottom around the annular element, and
   a plurality of curvilinear interconnecting elements, each curvilinear interconnecting element extending from a first end of a boomerang segment in an annular element to a second end of a boomerang segment in an adjacent annular element.

* * * * *